(12) United States Patent
Chadwick

(10) Patent No.: US 6,771,368 B1
(45) Date of Patent: Aug. 3, 2004

(54) LASER-INDUCED IONISATION SPECTROSCOPY, PARTICULARLY FOR COAL

(75) Inventor: Bruce Leonard Chadwick, Glen Iris (AU)

(73) Assignee: Generation Technology Research Pty Ltd., Mulgrave (AU)

( * ) Notice: Subject to any disclaimer, the term of this patent is extended or adjusted under 35 U.S.C. 154(b) by 0 days.

(21) Appl. No.: 09/763,907

(22) PCT Filed: Sep. 1, 1999

(86) PCT No.: PCT/AU99/00713

§ 371 (c)(1),
(2), (4) Date: Apr. 5, 2001

(87) PCT Pub. No.: WO00/14516

PCT Pub. Date: Mar. 16, 2000

(30) Foreign Application Priority Data

Sep. 4, 1998 (AU) .............................................. PP5730

(51) Int. Cl.⁷ .................................................. G01J 3/30
(52) U.S. Cl. ...................................... 356/318; 356/317
(58) Field of Search ................................ 356/318, 317; 250/253

(56) References Cited

U.S. PATENT DOCUMENTS

| | | | |
|---|---|---|---|
| 3,901,599 A | | 8/1975 | Meric |
| 4,486,894 A | | 12/1984 | Page et al. |
| 5,173,748 A | | 12/1992 | Billhorn |
| 5,757,484 A | * | 5/1998 | Miles .......................... 356/318 |
| 5,760,833 A | * | 6/1998 | Yang .......................... 348/323 |
| 5,813,543 A | * | 9/1998 | Gesing ........................ 209/653 |
| 6,069,689 A | * | 5/2000 | Zeng et al. .................... 356/73 |
| 2003/0218745 A1 | * | 11/2003 | Benicewicz et al. ........ 356/318 |
| 2003/0234928 A1 | * | 12/2003 | Lucas et al. ................. 356/318 |

FOREIGN PATENT DOCUMENTS

| | | |
|---|---|---|
| DE | WO 95/30140 | 11/1995 |
| EP | 0401 470 | 12/1990 |
| JP | 9-155293 | 6/1997 |
| JP | 10-38806 | 2/1998 |
| JP | 10-185817 | 7/1998 |

OTHER PUBLICATIONS

David Ottesen, "Laser diagnostics for research in coal combustion", SPIE Proceedings, 1375, pp. 124–132, 1990.*
Supplementary European Search Report on EP application 99947087.5 dated Aug. 5, 2003.
Proceedings of the SPIE—The International Society for Optical Engineering, vol., 1375, pp 122–123, 1990, ISSN 0227–786X (OTTESEN). Cited as Cagtegory "X" in the International Search Report.
IECEC–93. Proceedings of the 28th Intersociety Energy Conversion Engineering Conference, pp 995–1000, vol. 1, published Washington D.C. USA, 1993, 2 vol. (1262 + 9430 pp. ISBN 0841227225 (Singh et al), see Abstract. Cited as Cagtegory "X" in the International Search Report.

* cited by examiner

*Primary Examiner*—Drew A. Dunn
*Assistant Examiner*—Leo Boutsikaris
(74) *Attorney, Agent, or Firm*—Paul & Paul

(57) ABSTRACT

An apparatus for analyzing material, such as coal, comprises subjecting the coal (14) to laser light The laser light is used to vaporize and ionize a small amount of the coal to produce spectral emissions. A plurality of detection, (26, 30, 34) each of which detect a part of the spectrum of the spectrum emissions, collect spectral information and pass it to data collection means (38, 40, 42). The data is then analyzed to determine the presence and/or amount of one or more elements or species in the coal. In a preferred embodiment, the apparatus, has a plurality of data collection means (26, 30, 34), with each of the plurality of detection means being associated with a respective data collection means (38, 40, 42). The apparatus provides rapid and accurate analysis of the coal. The apparatus may be used to analyze coal on conveyor belt or coal in a seam in the ground.

20 Claims, 4 Drawing Sheets

LASER-INDUCED IONISATION SPECTROSCOPY, PARTICULARLY FOR COAL

BACKGROUND OF THE INVENTION

The present invention relates to an apparatus and method for analysing a material. The present invention is particularly suitable for analysing coal and for convenience the invention will hereinafter be described with reference to its application in analysing coal. However, it will be appreciated that the invention should not be considered to be restricted to the analysis of coal.

Coal is a fossil fuel source that has carbon and hydrocarbons as its main constituents. In addition, coal also contains lesser, although still significant, amounts of silicon, aluminium; iron, calcium, sodium, potassium and other elements. These species generally report to the ash after the coal has been combusted. Some coals, such as Victorian brown coals, also contain appreciable quantities of water.

It would be desirable to be able to analyse coal in two situations. The first of these involves analysis of the coal in-situ in the coal seam to assist in[] short term mine planning and to also be able to provide a more accurate estimate of the value of coal in the seam. The second application involves analysis of the coal shortly before or during combustion. This could assist in predicting the likelihood of fouling and slagging in a coal-fired boiler or combustor, thereby enabling preventative action to be taken. Fouling and slagging deposits are a major difficulty in the power generation industry and the severity of these deposits depends upon the inorganic constituents in the coal.

A number of techniques have been described that provide for coal analysis. Known analytical techniques for determining the composition of coal in a coal seam typically require the extraction of a sample or number of samples from the seam and returning the samples to a laboratory for conventional coal analysis of coal as described on page 9.4 of Perry et. al., "Chemical Engineer's Handbook", 5th Edition, McGraw Hill International Book Company, 1974.

U.S. Pat. No. 4,562,044, in the name of Bohl (assigned to The Babcock and Wilcox Company) describes a method and apparatus for the on-line analysis of a coal sample. The apparatus includes four radial arms each carrying a sample cup. An indexing motor indexes each sample cup along a circular path past a filling station where the cup is filled with pulverised coal. The cup then passes to an analysing station where various chemical analyses are performed. The cup then moves to a dumping station and a cleaning station, following which the cup is again ready for filling with pulverised coal.

U.S. Pat. No. 4,841,153 in the name of Wormald (assigned to Cogent Limited) relates to an analysis system and method for analysing coal in which the coal is bombarded by neutrons to generate gamma rays. The gamma rays are detected and the composition of the coal determined therefrom.

Other detectors bombard the coal with gamma rays or x-rays. Such systems require stringent safety precautions to be taken to avoid the possibility of exposing operating staff to x-rays or gamma rays.

Another technique that has been reported as being used on a laboratory scale for coal analysis is. laser-induced breakdown spectroscopy (LIBS) or laser spark emission spectroscopy. In this technique, a high energy laser (normally pulsed) is used to vaporise and ionise a small amount of material for analysis. The vaporised material or laser-induced breakdown plasma produces strong optical emission. Spectroscopic analysis of the optical emission gives information about the properties of the material being analysed. A discussion of one technique using LIBS is given in a paper by Ottesen et. al. entitled "Laser Spark Emission Spectroscopy for In-Situ, Real Time Monitoring of Pulverised Coal Particle Composition", published by Sandia National Laboratories (No. SAND 90-8586), on behalf of the Department of Energy, printed August 1990.

Although LIBS techniques have shown promise as being suitable for coal analysis, the present inventors are not aware of the technique being applicable beyond the laboratory scale, due to difficulties which include spectral line interference, slow sampling and response times, and calibration uncertainty.

SUMMARY OF THE INVENTION

It is an object of the present invention to provide an improved apparatus and method for the analysis of material.

In a first aspect, the present invention provides an apparatus for analysing a material comprising a laser for impinging laser light onto the material to vaporise and ionise at least part of the material and to cause spectral emissions therefrom, a plurality of detection means for detecting spectral emissions from the material, each of said plurality of detection means detecting a part of the spectrum of the spectral emissions, a plurality of data collection means to collect data from said plurality of detection means on said spectral emissions whereby each of the plurality of detection means is associated with a respective data collection means, and determining means to determine the presence and/or amount of one or more elements or species in the material.

Each of the plurality of detection means may comprise a spectrometer adjusted to a part of the spectral region. Each of the spectrometers may have a CCD detector associated with the spectrometer. The CCD detector may pass information on the spectral region to a data acquisition card or a data file in a computer or memory space. This data may then be analysed to determine the presence of one or more elements or species in the material and preferably to determine the amount or concentration of the element or species in the material.

Spectrometer types suitable for use in the present invention include grating and prism spectrographs; interferometers, such as etalon and scanning interferometer types; and filters, including coloured glass or interference filter types which allow transmission or reflection of a portion of the spectrum.

Detectors other than CCD's (charged-coupled detectors) may also be used. Other detectors that may be used in the present invention include photodiode arrays, vidicons, photomultiplier tubes and photodiodes. The person skilled in the art would readily appreciate which detector(s) should be used.

Preferably the apparatus further comprises control means for controlling firing of the laser and for controlling and synchronising operation of the plurality of detection means. The control means may include a timing circuit to fire the laser at specified times and to operate the detection means at other specified times. It is especially preferred that the control means also synchronises operation of each of the plurality of detection means such that the plurality of detection means simultaneously detect spectral emissions from the material.

In place of the timing circuit, the control means may comprise control software to control operation of the laser and the detection means.

The apparatus will also include one or more optical systems to focus the laser light on the material and to focus the spectral emissions on the plurality of detection means. The one or more optical systems may include one or more lenses, optical fibre, prisms, beam splitters or other optical components. Although suitable optical systems are required, it will be understood that the design of the optical system does not form part of the invention concept of the present invention and the person skilled in the art will be able to design a large number of suitable optical systems without requiring inventive ingenuity. Accordingly, the optical system(s) need not be discussed further.

The laser may be any laser capable of causing vaporisation and ionisation of a part of the material. Suitable lasers include solid state lasers such as the 1064 nm Nd:YAG laser, harmonic wavelengths of the Nd:YAG laser, i.e. 532 nm, 355 nm and 266 nm; gas lasers such as excimer lasers, e.g. 308 nm XeCl, or 248 nm KrF excimer lasers; carbon dioxide lasers; liquid lasers such as dye lasers; or any wavelength/frequency shifting, harmonic generation or mixing of the above. Lasers other than those specifically mentioned may also be used. The person of skill in the art will readily be able to select an appropriate laser.

The apparatus of the present invention may be suitable for analysing material in a laboratory, on a conveyor or in the ground.

The apparatus of the present invention enables high resolution of elemental fluorescence to be obtained and largely avoids or minimises spectral interferences common in known LIBS analysers. The present invention also enables detection of a large spectral range in a single laser pulse thereby greatly decreasing time for analysis. This reduced time for analysis allows the apparatus to be used as a real-time analytical tool. It also minimises sampling errors. In this regard, the apparatus can obtain an analysis of a number of elements in that portion of the material vaporised in each laser pulse. In contrast, known LIBS apparatus required sequential analysis of the material which meant that a number of laser pulses were required. Each laser pulse would vaporise a different part of the material which could lead to errors, particularly if the material being analysed has pronounced heterogeneity.

The present invention also relates to a method for analysing a material.

In a second aspect, the present invention provides a method for analysing a material comprising subjecting said material to laser light to at least partly vaporise and ionise said material to thereby cause spectral emissions, detecting said spectral emission with a plurality of detection means, each of said plurality of detection means detecting a part of the spectrum of the spectral emission, collecting data from a plurality of detection means and analysing said data to determine the presence and/or amount of one or more elements or species in the material wherein the step of collecting data from the plurality of detection means comprises passing spectral information from the plurality of detection means to data acquisition cards associated with each of the plurality of detection means.

The method may further comprise controlling operation of the laser and the plurality of detection means.

DESCRIPTION OF THE DRAWINGS

The apparatus and method of the present invention will now be further described with reference to a preferred embodiment of the present invention. In the accompanying drawings.

Figure 1:
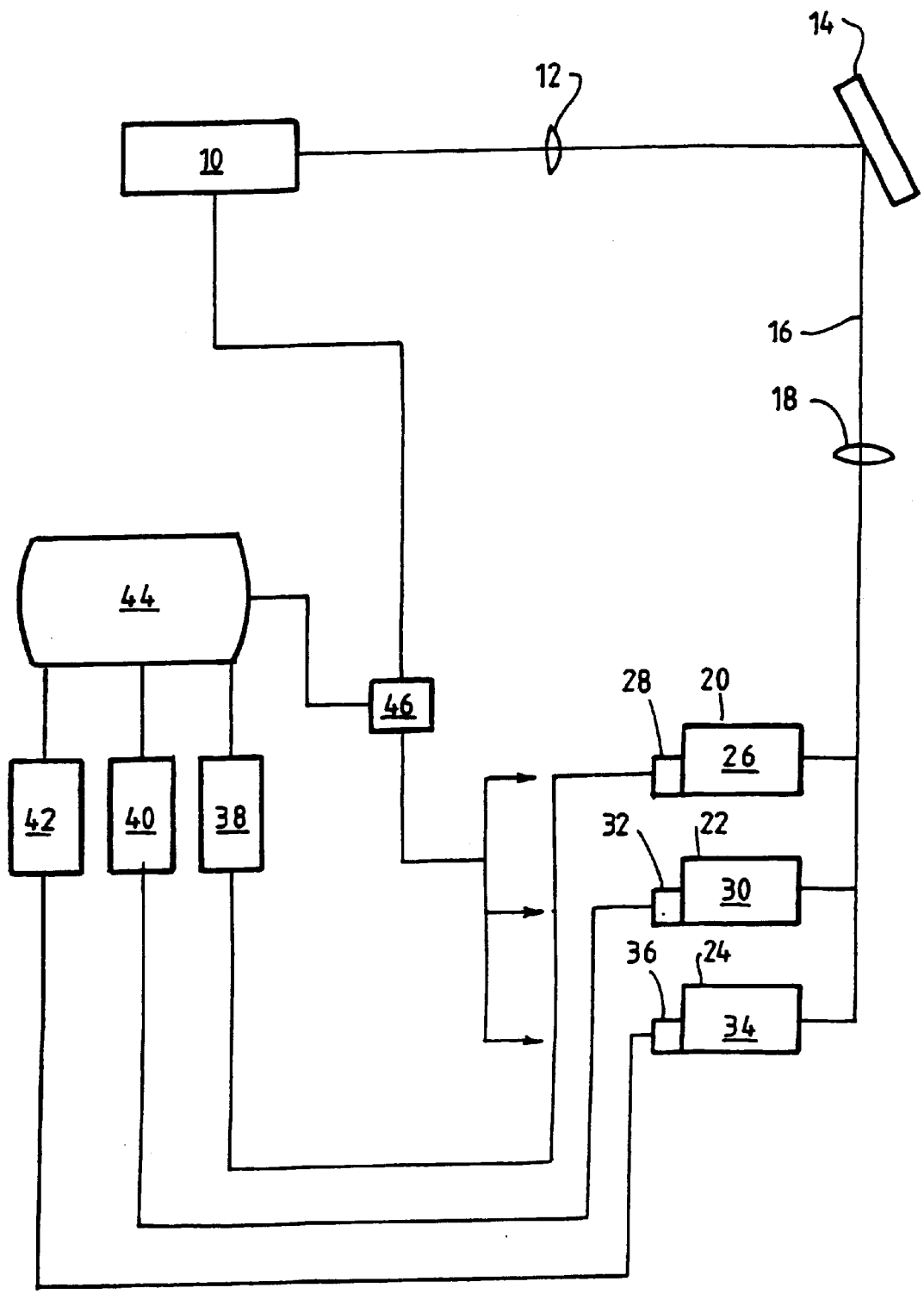
FIG. 1 is a schematic drawing of an apparatus in accordance with an embodiment of the present invention.

DETAILED DESCRIPTION OF THE INVENTION:

In the following description of a preferred embodiment of the present invention, the method and apparatus of the invention was used to analyse coal. However, it will be appreciated that the method and apparatus of the present invention may be used to analyse a wide range of materials. The materials that may be analysed by the method of the invention may be solid, liquid or even gaseous. In the apparatus shown in FIG. 1, a laser 10, which may be a 1064 nmNd:YAG laser, emits pulses of laser light that are focused by an optical system 12 onto a material to be analysed 14. In the small region of the laser spot focused on the material 14, the laser power density produces rapid heating and ionisation of a small sample of the material. Light is emitted from the vaporised and ionised material containing spectral information on the material involved. The light emitted from the vaporised and ionised material is schematically represented at 16 and this emitted light 16 is passed through objective lens 18 and then is detected by a plurality of detection means 20, 22, 24. The apparatus shown in FIG. 1 has three detection means but it will be appreciated that a lesser or greater number of detection means may be utilised. It is envisaged that a greater number of detection means may be utilised if especially high resolution is required. Detection means 20 comprises a spectrometer 26 that is adjusted to a part of the spectrum of the spectral emissions emanating from material 14. Detection means 20 also includes a CCD detector 28 which suitably comprises a readily available commercial CCD detector. The CCD detector 28 may comprise a 12–16-bit detector.

Similarly, detection means 22 comprises a spectrometer 30 and a CCD detector 32. Detection means 24 also comprises a spectrometer 34 and CCD detector 36.

The CCD detectors 28, 32, 36 detect information from the specific spectral region provided by their associated spectrometers. The CCD detectors then pass the detected information to respective dedicated data acquisition cards 38, 40, 42 which are associated with a central computer 44. The data acquisition cards may include analog-to-digital conversion boards/circuitry. The computer 44 also includes control means 46 to control the operation of the laser 10 and the plurality of the detection means 20, 22, 24.

In use of the apparatus shown in FIG. 1, the control means 46 sends a control signal to laser 10 which causes the laser to emit a pulse of laser light. The pulse of laser light 10 is focused onto the surface of material 14 which causes vaporisation and ionisation of a small part of the material 14.

Shortly after the control signal causes a pulse of laser light 10 to be emitted by the laser, the control means 46 sends control signals to the detection means 20, 22, 24 which turns on those detection means. It is preferred that there is a slight delay between firing of the laser and initialisation of operation of the spectrometers in order to ensure that the CCD detectors do not detect the pulse of laser light and only detect the emitted spectra. This control signal causes the spectrometers 26, 30, 34 to collect light from the relevant spectral region for a predetermined period of time and to enable the CCD detectors 28, 32, 36 to detect that light. Each of spectrometers 26, 30, 34 collect light from particular regions of the emission spectrum. The particular regions may be discrete, separate regions of the spectrum, or there may be some overlap between the spectral region collected by one of the spectrometers and the spectral region collected by another of the spectrometers. Whilst the detection means 20, 22, 24 are collecting and detecting the light from the emitted spectral region from the sample 14, the CCD detectors are also forwarding information to the respective data acquisition cards 38, 40, 42. The CCD detectors are formed from individual areas of light sensitive material (usually silicon) known as pixels. Each pixel converts the light intensity to an electric change or current which is then digitised by the data acquisition cards. The use of separate data acquisition cards for each detection means enables rapid collection of large amounts of data and this in turn allows the rapid analysis of the material to take place at high spectral resolution.

The data collected by the data acquisition cards 38, 40, 42 is then analysed by the computer to determine the elements or species present in the material and also to determine the relative amounts of each of those elements or species. The amount of each element or species in the material may be determined by integrating the area under the spectral line at a wavelength that is characteristic of the spectral emission of a given element or species and comparing that area with the area under the same spectral line obtained from a material having a known content of that particular element or species.

Figure 2:
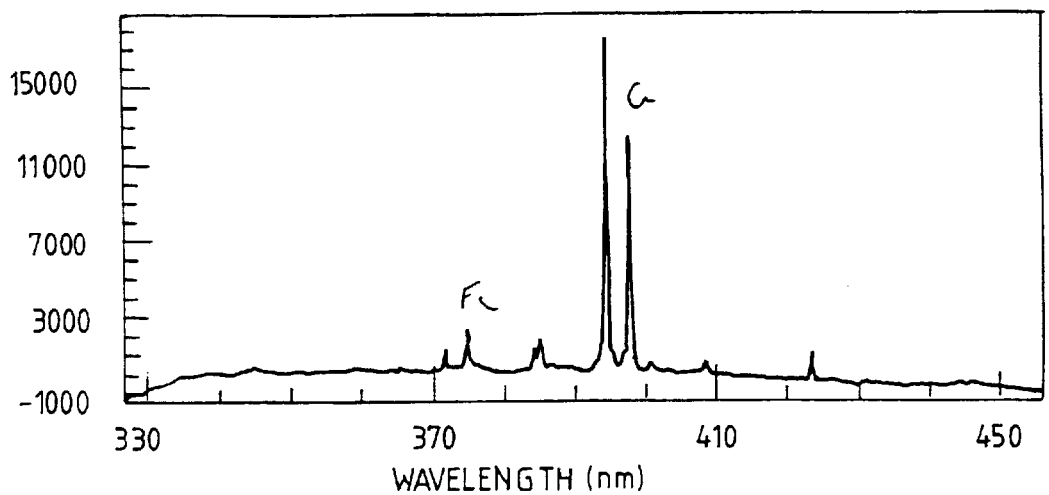
FIG. 2 shows an analysis of coal obtained using the apparatus in accordance with the present invention.
Figure 2:
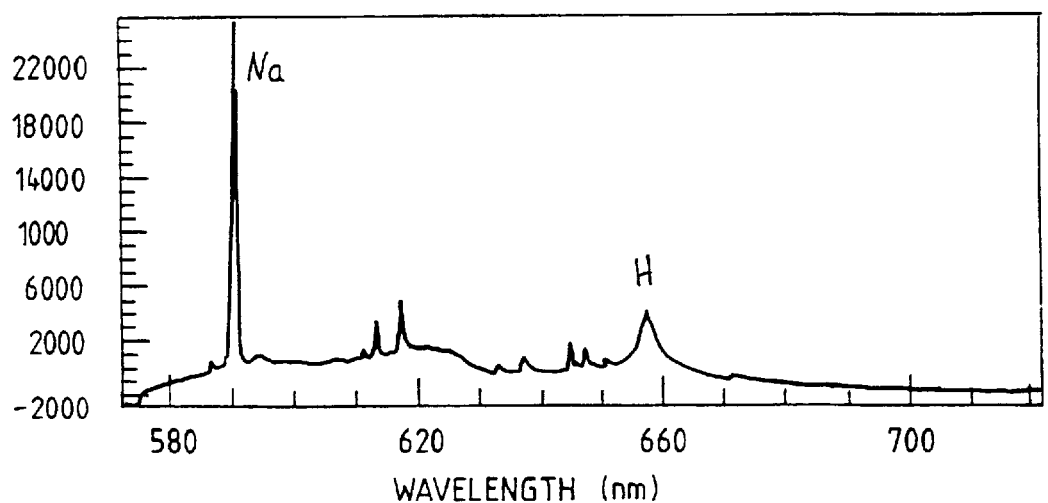
Figure 2:
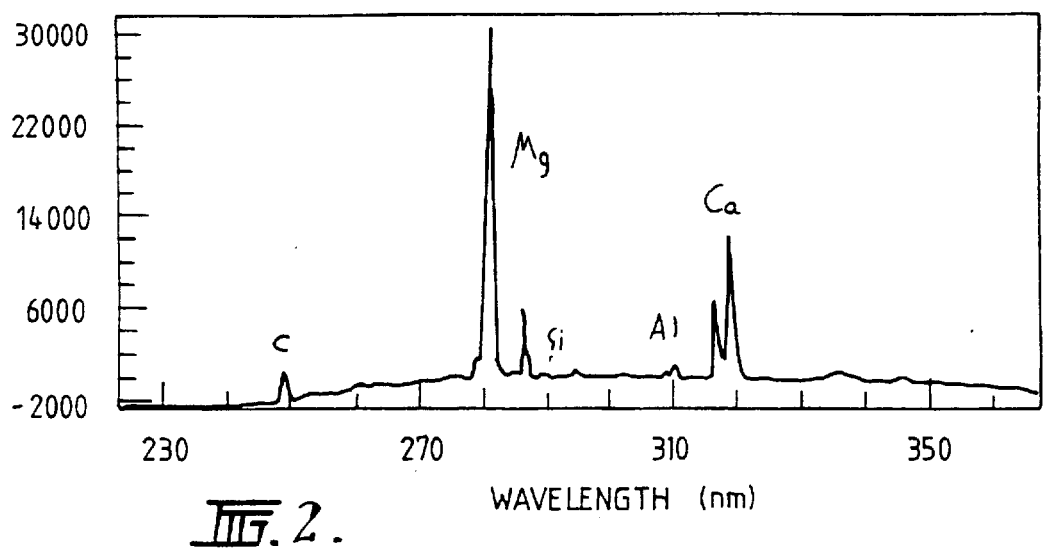

Print outs of the spectral emission data collected from an apparatus in accordance with the present invention is shown in FIG. 2. FIG. 2 has been marked to show the spectral lines for ion, calcium, sodium, hydrogen, carbon, magnesium, silicon, and aluminium.

Since the apparatus allows the measurement of coal components including carbon (C), hydrogen (H) and oxygen (O)—as well as ash forming components,—it also allows determination of fuel properties relevant to utilisation of the coal, in particular the coal heating (calorific) value and water content.

The apparatus and method of the present invention preferably detects spectral emissions from the material being analysed in the visible light range. However, the apparatus may also detect long wavelength infrared and short wavelength ultra violet radiation.

The apparatus of the present invention provides an apparatus that enables high resolution determination of a range of materials. Detection of a large spectral range in a single laser pulse is possible, which greatly reduces the time taken for analysis. This in turn leads to a reduction in sampling errors because all of the elements being analysed are present in that portion of the sample vaporised in each laser pulse, compared to the laser vaporising different pieces of sample when elements are analysed sequentially. Although a single pulse of laser is sufficient to enable analysis of a wide range of elements in the material, sound sampling techniques will utilise information collected and analysed from a plurality of laser pulses. For example, twenty to one hundred laser pulses may be used to increase the amount of data collected from the material and thereby obtain a more accurate analysis.

Furthermore, use of a plurality of CCD detectors enables relatively short CCD detector arrays to be used, which reduces the transfer time of data from the CCDs to the computer when compared to configurations using very long CCD arrays. Moreover, the apparatus provides good dynamic range. Dynamic range is an important concept in any analytical instrument. Ideally, instruments are designed to detect dilute concentrations of elements or compounds. However, they need to be designed so that they can determine high concentrations as well, thus widening their potential applications. In the present apparatus, the dynamic range is determined by two factors.

Firstly, the dynamic range is determined by the sensitivity of the spectrometer system. This is a function of the sensitivity and resolution of the CCD's plus the level of light transmittance to the detector (which may be adjustable by the use of filters, for example).

The second method of adjusting dynamic range is related to the power of the laser. The sensitivity of the technique (i.e. the detection limit) is critically dependent on laser power. Adjusting the laser power therefore offers a convenient way of widening the dynamic range available to the user. Adjustment of the laser power in the present apparatus may be conducted by varying the timing or control circuitry or by a number of other methods available to the instrument designer. This is a further advantage of the present invention.

It will be appreciated that the invention described herein may be susceptible to a number of variations and modifications other than those specifically described. In particular, although FIG. 1 shows the use of multiple spectrometers, a single multi-channel spectrometer may be used. However, each channel of such a multi-channel spectrometer would have a dedicated CCD detector (or other suitable detection means) associated therewith.

The optical systems used to focus the laser light onto the sample and to focus the emitted light onto the detection means may be of any particular design and still fall within the scope of the present invention.

The apparatus of the present invention can be used as a laboratory instrument or as an in-field instrument. The apparatus and method of the present application analyse emitted light and not reflected light and thus it is not necessary that the surface of the material being analysed be exactly aligned with the light collection optical system. This allows the apparatus to be used in situations where sample preparation is not critical. With particular regard to its use in coal analysis, the in-field instrument may be used to analyse coal travelling on a conveyor belt. In this system, the laser may directly impinge upon coal travelling along the conveyor belt, with the detection means arranged to detect the spectral emissions from the material on the conveyor belt. Alternatively, a sampling apparatus may remove a sample of coal from the conveyor belt for analysis by the apparatus in close proximity to the conveyor belt to thereby provide a real time analysis of the coal on the conveyor belt. It is also to be understood that the present invention can be used to analyse materials other than coal in the field.

The apparatus may also be used as an in-hole or in-ground instrument for analysing coal in coal seams. In this embodiment, a sampling head may be lowered down a hole bored in the coal seam. Alternatively, if the coal seam is relatively soft, the sampling head may be included as part of a penetrometer or other penetrating instrument that is pushed into the coal seam. The Sampling head may be optically linked to the detection means by an optical system that includes one or more optical fibres such that the detection means can be located remotely from the sampling head. This allows the size of the sampling head to be minimised Turning now to FIG. 3, an in-ground analyser includes laser analysis system 50 that includes a laser. Fibre optic cable 51 is linked to lens system 52 and allows laser light from laser analysis system 50 to be passed to the zone of material to be analysed. A bore hole 54 is either pre-drilled in the ground or formed by a penetrometer.

The optical fibre cable 51 and lens system 52 are housed within a strong housing 55 that is inserted into the bore hole 54. Housing 55 includes a clear window 53 located adjacent lens system 52. This is more clearly shown in the inset in FIG. 3. This allows the laser light to impinge upon the coal adjacent the clear window 53 to form a plasma. The emission spectra of the plasma is returned via fibre optic cable 51 to the laser analysis system 50 for analysis. The laser analysis system 50 is, in this regard, essentially identical to the apparatus as shown in FIG. 1.

Figure 3:
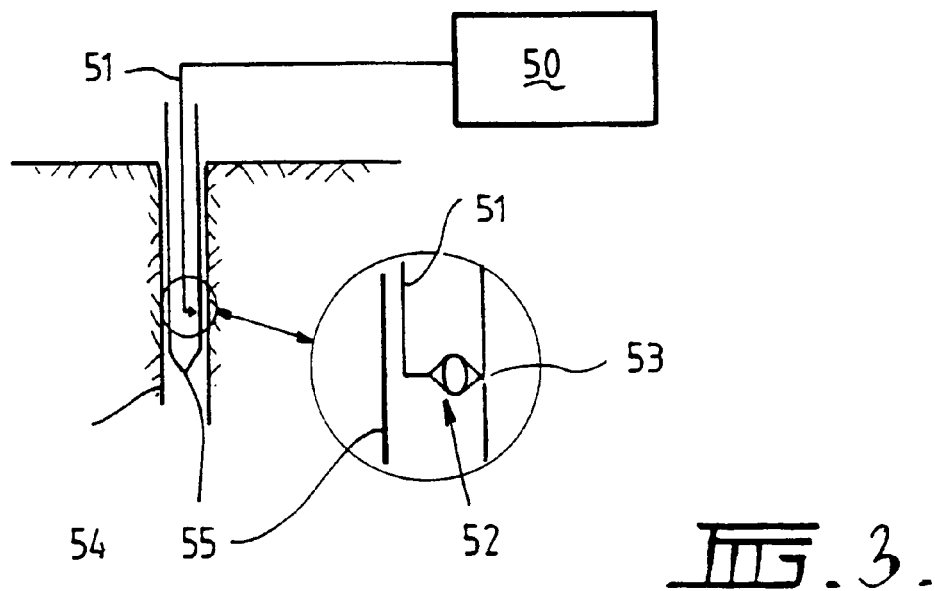
FIG. 3 shows an arrangement incorporating the present invention for in-situ analysis of coal.

As an alternative to the embodiment shown in FIG. 3, the laser can be directly mounted in housing 55 and lowered into the ground.

Figure 4:
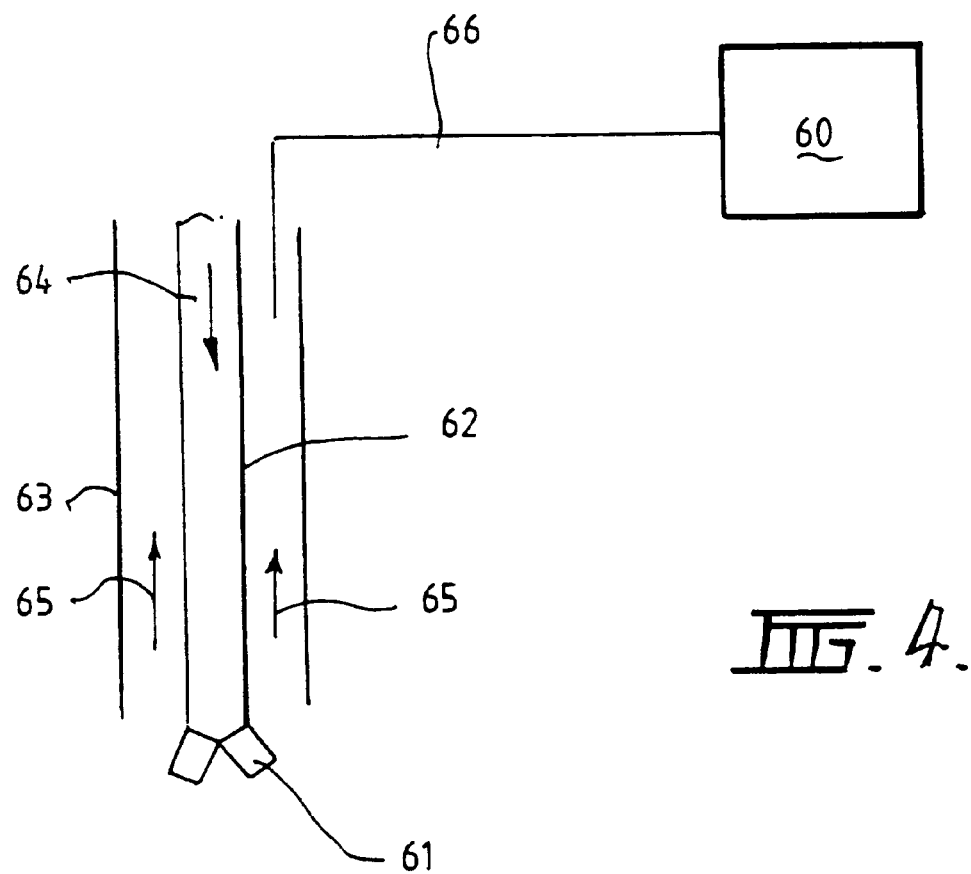
FIG. 4 shows an alternative arrangement for analysing coal in a coal seam.

FIG. 4 shows an alternative apparatus for in-situ analysis. The apparatus includes a laser analysis system 60 that is essentially identical to that shown in FIG. 1. In order to analyse material from the ground, a drill bit 61 and drill stringer 62 excavate a bore hole 63. Compressed air is passed downwardly through drill stringer 62 (with the direction of air flow in drill stringer 62 being shown by arrow 64) and subsequently moves upwardly through the annular space defined between the outer wall of drill stringer 62 and bore hole 63, as shown by arrows 65. The upward flow 65 of air entrains cuttings from drill bit 61 and these cuttings are then delivered to laser analysis system 60 for analysis. Delivery of the cuttings is shown schematically by reference numbered 66.

Figure 5:
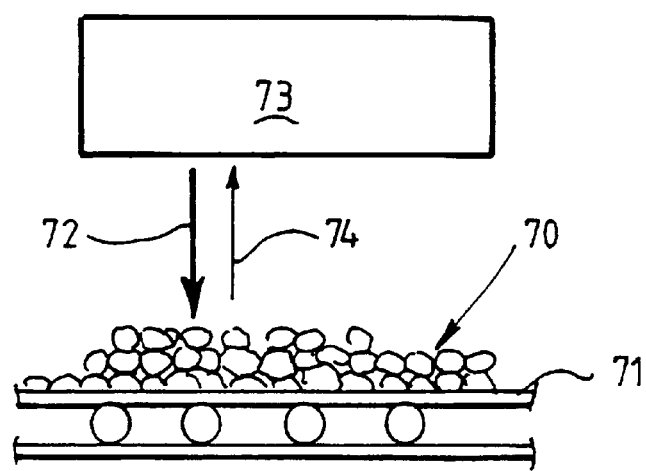
FIG. 5 shows an embodiment of the present invention being used for on-conveyor analysis.

Analysis of coal on a conveyor belt is shown schematically in FIG. 5. In this Figure, a layer of coal 70 travelling on conveyor belt 71 is subjected to a laser beam 72 emanating from laser analysis system 73. Laser analysis system 73 is essentially identical to the apparatus shown in FIG. 1. The fluorescence spectra 74 emitted from the coal is then analysed by laser analysis system 73.

Figure 6:
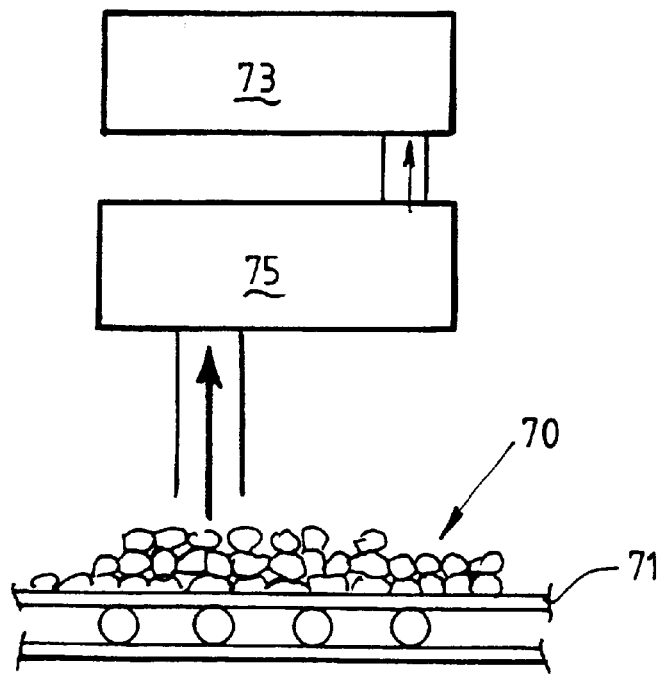
FIG. 6 shows an alternative arrangement of the present invention for on-conveyors analysis of coal.

An alternative apparatus for analysing coal on a conveyor is shown in FIG. 6. In FIG. 6, features in common with FIG. 5 are denoted by the same reference numerals as FIG. 5. The apparatus of FIG. 6 differs from that of FIG. 5 in that the apparatus of FIG. 6 includes a sampling system 75 that extracts a sample of coal from the conveyor, which sample is subsequently analysed by the laser analysis system 73. After analysis, the sample is returned to the conveyor and a fresh sample is taken for analysis.

Those skilled in the art will appreciate that the invention described herein is susceptible to variations and modifications other than those specifically described. It will be understood that the present invention encompasses all such variations and modifications that fall within the spirit and scope.

What is claimed is:

1. An apparatus for analysing a material, comprising:
   a laser for impinging laser light onto the material to vaporise and ionise at least part of the material and to cause spectral emissions therefrom;
   a plurality of spectrum detection means for detecting spectral emissions from the material, each of said plurality of detection means detecting a part of the spectrum of the spectral emissions;
   a plurality of data collection means, each of the plurality of detection means being associated with a respective one of the plurality of spectrum detection means such that each of the plurality of data collection means collects data from its associated spectrum detection means;
   control means for controlling the firing of the laser and for controlling and synchronising the operation of the plurality of the spectrum detection means simultaneously to simultaneously detect the spectral emissions from the material across the spectrum of spectral emissions; and
   determining means connected to each of said plural data collection means for receiving data collected thereby for determining the presence and amount of one or more elements or species in the material, said determining means simultaneously analysing the data collected by each of the data collection means.

2. Apparatus as claimed in claim 1, wherein each of the plurality of spectrum detection means comprises a spectrometer adjusted to detect a contiguous part of the spectral region.

3. Apparatus as claimed in claim 2, wherein each of the plurality of spectrum detection means comprises a spectrometer adjusted to detect a contiguous part of the spectral region and to detect an overlapping portion of an adjacent part of the spectral region.

4. Apparatus as claimed in claim 2, wherein the spectrometers are selected from grating and prism spectrographs, interferometers including etalon and scanning interferometers, and filters including coloured glass or interference filters which allow transmission or reflection of a portion of the spectrum.

5. Apparatus as claimed in claim 1 wherein, each data collection means comprises a data acquisition card; wherein said plurality of spectrum detection means includes a plurality of spectrometers; wherein said control means controls the simultaneous operation of said plural spectrometers; and wherein said control means simultaneously turns on said plural spectrometers at a short time after said laser is fired, said plural spectrometers being otherwise turned off.

6. Apparatus as claimed in claim 1, wherein each of said plurality of spectrum detection means comprises a spectrometer having a CCD detector associated therewith, wherein each data collection means comprises a data acquisition card circuit, and wherein each data acquisition card circuit receives data from the respective CCD detector associated therewith.

7. Apparatus as claimed in claim 1, wherein the control means includes a timing circuit to fire the laser at specified times and to turn on the detection means at other specified times thereafter.

8. Apparatus as claimed in claim 1, wherein the control means operates under the direction of control software to send a control signal which causes the laser to emit a pulse of laser light and to send a control signal to each of the plurality of spectral detection means which turns on said spectral detection means.

9. Apparatus as claimed in claim 1 further comprising an optical system having a first portion for focusing laser light on the surface of the material for creating a plasma emitted light and having a second portion for collecting said spectral emissions and for focusing the spectral emissions on the plurality of detection means wherein the surface of the material is free of alignment with said second collecting portion of said optical system.

10. Apparatus as claimed in claim 1, wherein the laser is selected from the group comprising solid state lasers including 1064 nm Nd:YAG lasers, harmonic wavelengths of the Nd:YAG laser being 532 nm, 355 nm and 266 nm, gas lasers including excimer lasers, 308 nm XeCl and 248 KrF excimer lasers, carbon dioxide lasers, liquid lasers including dye lasers, and any wavelength/frequency shifting laser with harmonic generation or mixing thereof.

11. Apparatus as claimed in claim 1, wherein the spectrum detection means is selected from the group comprising photodiode arrays, vidicons, photomultiplier tubes and photodiodes; and wherein said spectrum detection means is capable of detecting emissions in the infrared, visible light and ultraviolet ranges.

12. Apparatus as claimed in claim 1, wherein said laser impinges upon material traveling on a conveyor belt to thereby effect analysis of the material on the conveyor.

13. Apparatus as claimed in claim 1, wherein the apparatus comprises an in-hole or in-ground instrument for analysing material in the ground.

14. Apparatus as claimed in claim 13, wherein the apparatus includes a sampling head for being lowered down a hole.

15. Apparatus as claimed in claim 13, wherein the apparatus includes a sampling head carried within a penetrometer or other ground penetrating instrument.

16. Apparatus as claimed in any one of claims 14–15, wherein the sampling head is optically linked to the detection means by an optical system that includes one or more optical fibres wherein the detection means is located remotely from the sampling head.

17. An apparatus to analyze material by laser induced breakdown spectroscopy (LIBS), comprising:

a laser for impinging laser light onto a material to create spectral emissions as a function of the elements present thereon;

a plurality of spectrometer means operating in parallel, each of said plural spectrometer means detecting a predetermined contiguous part of the spectrum of spectral emissions;

a plurality of data acquisition circuits, connected one each to a respective one of said spectrometer means for collecting spectral data from said connected spectrometer means;

controller circuit means connected to said laser and to each of said spectrometer means for controlling the firing of a laser pulse and at a selected time thereafter for simultaneously triggering on each of said plural spectrometer means for detecting said spectral emissions; and computer means connected to each of said data acquisition circuits for receiving said spectral data collected when each of said spectrometer means is simultaneously triggered on, said computing means analyzing said spectral data.

18. The apparatus of claim 17, wherein said plural spectrometer means and said plural data acquisition circuits are adjusted for values in the visible light range.

19. The apparatus of claim 17, wherein said plural spectrometer means and said plural data acquisition circuits are adjusted for values in the infrared, visible light, and short wavelength ultraviolet range.

20. The apparatus of claim 17, wherein said laser is triggered on by said controller circuit means, wherein each of the spectrometer means is simultaneously triggered on for a pre-selected period of time; wherein each spectrometer means includes a spectrometer and a CCD detector connected to said spectrometer; wherein a respective one of said data acquisition circuits is connected to a respective CCD detector; wherein said controller circuit means is also connected to said computer means, the operation of said controller circuit means being directed by software resident in said computer means; and wherein said controller circuit means is also connected to each of said CCD detectors to simultaneously trigger on each for said pre-selected period of time.

* * * * *

UNITED STATES PATENT AND TRADEMARK OFFICE
CERTIFICATE OF CORRECTION

PATENT NO. : 6,771,368 B1
DATED : August 3, 2004
INVENTOR(S) : Bruce Leonard Chadwick It is certified that error appears in the above-identified patent and that said Letters Patent is hereby corrected as shown below:

<u>Title page,</u>
Item [57], ABSTRACT,
Line 2, insert a period -- . -- after the words "coal (14) to laser light";
Line 5, the words "of the spectrum" should only appear once;
Line 10, delete the comma "," after the word "apparatus";

<u>Column 1,</u>
Line 24, delete the brackets "[]" after the word "in";

<u>Column 7,</u>
Line 2, insert a period -- . -- after the word "minimised";
Line 3, insert an indent at the beginning of the sentence indicating a new paragraph;

<u>Column 8,</u>
Line 48, should read -- Apparatus as claimed in claim 1 --.

Signed and Sealed this

Twelfth Day of October, 2004

JON W. DUDAS
*Director of the United States Patent and Trademark Office*